United States Patent [19]

North, Jr. et al.

[11] Patent Number: 4,642,094
[45] Date of Patent: Feb. 10, 1987

[54] NON-SURGICAL EMBRYO TRANSFER DEVICE

[76] Inventors: Walter L. North, Jr.; Barry M. England, both of R.D. 1, Box 454, New Enterprise, Pa. 16664

[21] Appl. No.: 615,072

[22] Filed: May 29, 1984

[51] Int. Cl.$^4$ ............................................. A61M 1/00
[52] U.S. Cl. ...................................... 604/55; 604/73; 604/218
[58] Field of Search ................. 128/1; 604/53, 55, 73, 604/93, 181, 218, 264

[56] References Cited

U.S. PATENT DOCUMENTS

| | | | |
|---|---|---|---|
| 840,472 | 1/1907 | Brookes | 604/218 |
| 2,572,155 | 10/1951 | Hoyt | 604/218 |
| 3,757,781 | 9/1973 | Smart | 604/218 X |
| 4,173,227 | 11/1979 | Cassou et al. | 604/218 |
| 4,474,576 | 10/1984 | Gobby | 604/264 X |

Primary Examiner—Stephen C. Pellegrino
Attorney, Agent, or Firm—Thomas E. Sterling

[57] ABSTRACT

This invention is a veterinary instrument for non-surgically implanting in an animal's uterus a live embryo for the purpose of inducing pregnancy. The device is comprised of a tip element having a small, medium and large diameter bore partially therethrough, an exit passage in communication with the small diameter bore terminating at a laterally positioned countersunk exit hole. An embryo containing straw is positioned within and compressed by the medium diameter bore. The tip is screw connected to a plunger element having a rod therethrough which is adapted to fit within the embryo containing straw and to force the contained embryo out of the countersunk hole. A modification of the instrument includes a thumbscrew positioning ring on the end portion of the plunger element adapted to mark the position of the countersunk hole so that it may be properly oriented when it is within the animal.

10 Claims, 6 Drawing Figures

NON-SURGICAL EMBRYO TRANSFER DEVICE

PRIOR ART STATEMENT

The inventor knows of no uncited prior art anticipating this invention. The inventor is not withholding known prior art which he considers to anticipate this invention.

This invention relates to medical or veterinarian instruments, and in particular to a non-surgical embryo transplant instrument.

The transplant of embryos into animal host is a well known veterinary technique. It in general consists of the insertion of an elongated instrument through the animal's vagina, cervix, and into the horn of the uterus where an embryo is discharged. This has been done in the past by plunger type devices into which are inserted standard plastic insemination straws containing the embryo in a vehicle liquid. The plastic straws are inserted into plastic or metal devices which are fitted onto a plunger type mechanism which forces the contents of the straw through the front end of the instrument and into the host animal.

One disadvantage and problem of some prior devices is that the straw does not fit tightly into the tip of the device. When the fluid is ejected from the straw, it may leak around the edge of the straw rather than be expelled. In addition, mucus and tissue from the animal's cervix and uterus may gather around the end of the straw decreasing the effectiveness of the procedure.

This invention solves this problem by a special "lock-in" feature consisting of a small bore restriction at the end of the tip's main bore into which the end of the straw fits snugly. This feature insures that no leaks occur between the straw end and the tip.

Other devices used for embryo transfer have had larger diameter tips and plungers making insertions into the cervix and uterus of the host animal difficult. This invention features a smaller diameter instrument, which insures that there is less trauma when passing the device through into the uterus. Since this device is smaller in diameter it can be used. on virgin heifers and smaller animals which cannot easily be penetrated by the larger diameter instruments presently used.

The tip of the present invention is rounded, hand polished, and has a smooth countersunk exit hole inducing less trauma when the instrument is inserted into the uterus of the host animal. Because of these features, there is less trauma, less damage to the uterus, and should be a better rate of pregnancy obtained with the present device than those presently in existence.

There are in existence transfer devices constructed of large diameter plastic with an exit hole in the front area of the tip. Such devices induce more trauma when inserted because of their large diameter. In addition, the plastic devices gather more debris in the front facing exit hole. This feature adversely affects the pregnancy rate. This invention has a tip which discharges the embryo from its side portion, thus eliminating this disadvantage.

Furthermore, such plastic devices lack stiffness, making insertion more difficult. This increases the chance of damage to the uterine parts and decreases the pregnancy rate. The device of this invention is constructed wholly of stainless steel having the necessary stiffness and small diameter for advantageous application.

An object of this invention is to provide an embryo transfer device tip whose threads are interchangeable and will fit any of the plunger portions of our devices. An advantage of the present invention is, therefore, that it is possible for the operator to use several tips and a few of the plunger sections. Since only the outside part of the tube plunger section comes in contact with the cervix or uterus, it can be chemically sterilized between transfers. Several tips can be steam sterilized ahead of time for absolute sterility (since the embryo and medium will come in contact with part of the inside of the tip). The tips can then be loaded by locking in pre-sterilized standard ¼ cc artificial insemination straws already loaded with the embryo and medium for transfer.

This feature makes the device advantageous to the operator in the way of cost efficiency. He can buy as many tips as he needs, but needs to buy fewer of the tube plunger sections since he can fit any of the highly sterilized tip sections onto any of the tube plunger sections.

An object of this invention is to provide an embryo transfer device having a tip that will compress the end of the embryo containing straw forming a fluid type seal between the straw and the tip. This constitutes the "lock-in" feature of this device.

It is yet another object of this invention to provide an embryo transfer device of small diameter which will cause less trauma when passing into the body of the host animal.

It is still another object of this device to provide a smooth, countersunk, small side delivery passage for the embryo whereby debris does not enter the exit chamber or passage in front of the straw.

It is still another object of this invention to provide an embryo transfer device which can be easily cleaned, washed out, and sterilized.

It is still another object of this invention to provide an embryo transfer device having a marking device which may be oriented in the same direction as the exit orifice or passage whereby the exit orifice may be easily oriented inside of the host prior to ejection of the embryo.

These and other features of this invention are more clearly set forth in the following specification, claims, and drawings, in which:

Figure 1:
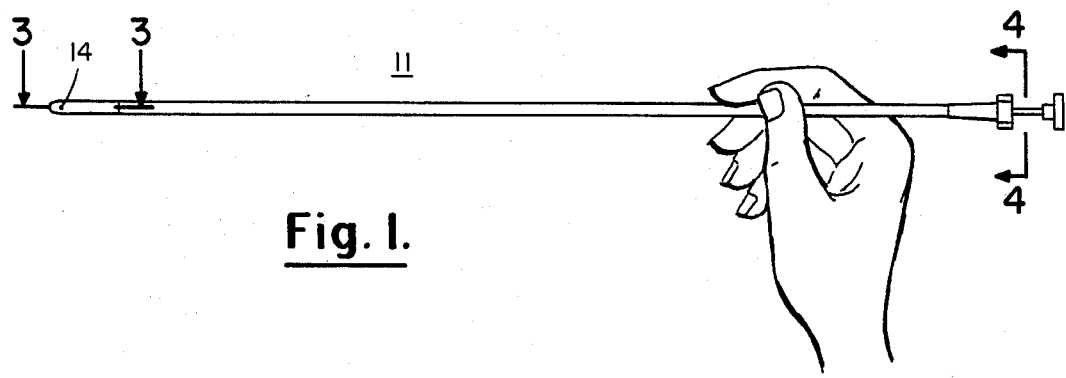
FIG. 1, is a third dimensional view of the invention tip coupled to a plunger device.
Figure 2:
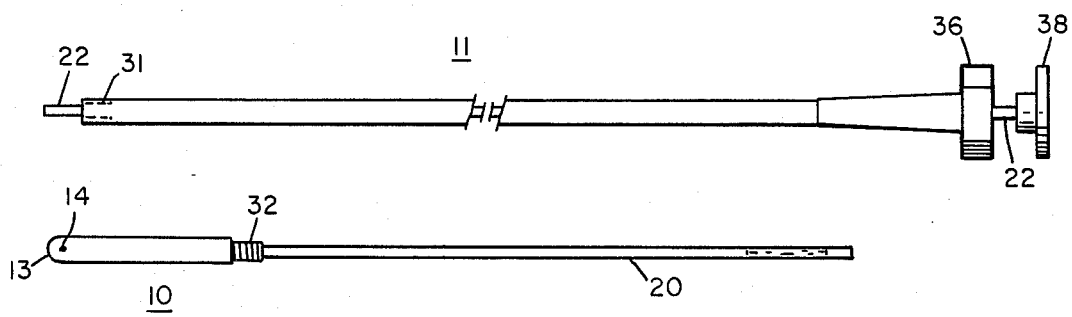
FIG. 2, is a third dimensional view of the device showing the rear and tip sections in a disassembled position, with an embryo containing standard insemination straw extending from the tip section.
Figure 3:
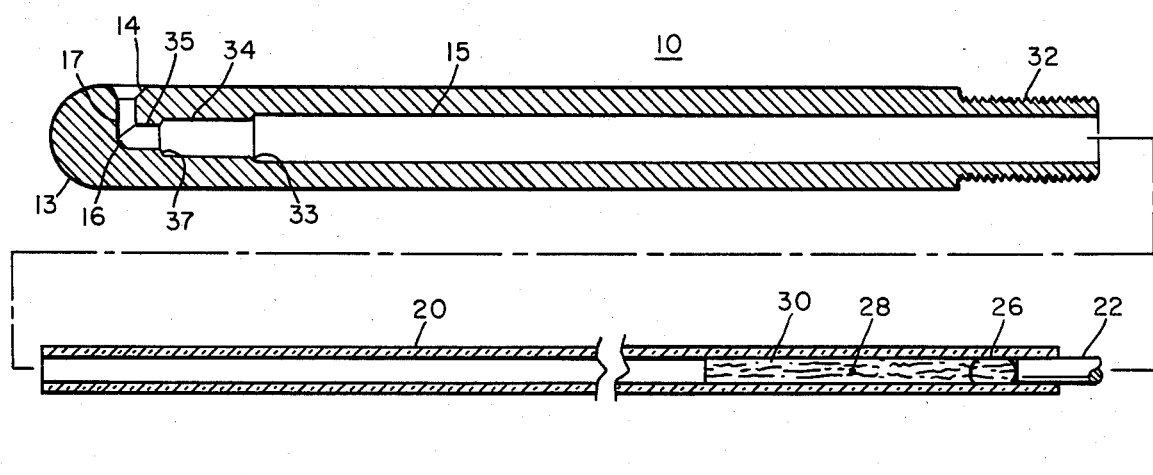
FIG. 3, is a longitudinal cross sectional view of the tip-plunger section of the device and the embryo containing straw taken along lines 3—3 of FIG. 1.
Figure 3:
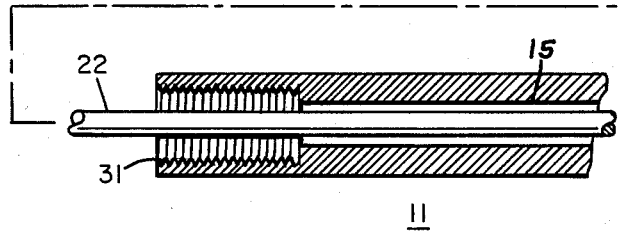
Figure 4:
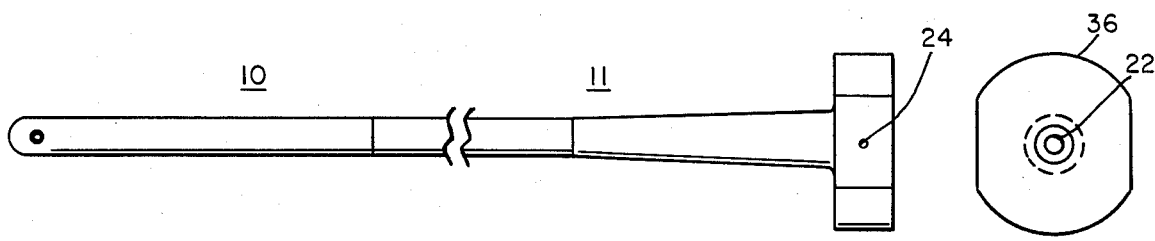
FIG. 4, is a top and side view of the plunger portion of the device taken along lines 4—4 of FIG. 1.

Referring now to the drawings and in particular to FIGS. 1 and 2, 10 represents the elongated front tip element of the device screw connected with plunger element 11 in the rear portion. Tip 10 is the portion which is first inserted within the host animal. Plunger element 11 is the forcing device which propels the embryo and fluid out of an orifice 14 located on the side portion of tip 10 and into the uterus of the host animal.

Tip 10 is comprised of a hollow stainless steel cylinder, which can be of various lengths and of suitable diameter to fit on the size threads of and screw into plunger element 11. Tip 10 has a solid rounded forward end section 13 which is highly polished so that the instrument does not damage the cervix or uterine mucosal wall while it is manualy passed therein. The rear end portion of tip 10 has an extended threaded male section 32 thereon adapted to screw on a mating threaded female section 31 of the forward end of plunger element 11. A longitudinal bore 15 extends through the rear portion of the tip 10 and through the forward portion of the plunger element 11 as well.

Longitudinal bore 15 narrows into a smaller medium diameter bore 34 which subsequently narrows into a small diameter bore 35, terminating at the exit chamber 16 at the forward portion of tip 10. The first shoulders 33 between the longitudinal bore 15 and medium diameter bore 34 have an angle of about 34° with the horizontal, as do the second shoulders 37 between the medium diameter bore 34 and the small diameter bore 35. This angle may vary plus or minus 10° and is generally the angle of the drill which is used to shape the particular bores. Straw 20 is a hollow cylinder comprised of plastic material of a diameter that will slide into longitudinal bore 15. The medium diameter bore 34 is slightly smaller than straw 20 which is inserted therein, so that when the straw 20 is forced into the medium diameter bore 34, it is compressed forming a fluid type seal. The straw 20 will abut the shoulders 37 between the medium diameter bore 34 and the small diameter bore 35 and remain fixed thereon. This is the "lock-in" feature of the device.

Small diameter bore 35 terminates at an exit chamber 16 connected to an exit passge 17 which leads to countersunk orifice 14. Countersunk orifice 14 is countersunk beneath the surface of tip 10 and the surface about it smoothed.

The plastic straw 20 contains an embryo 28 within a liquid vehicle medium 30 and is inserted in longitudinal bore 15. Straw 20 is then pressed forward into the medium diameter bore 34 which compresses the end portion of said straw 20, thus forming a seal through which no fluid will pass. The straw 20 then abuts the shoulders 37 between the medium diameter bore 34 and the small diameter bore 35. Small diameter bore 35 is sufficiently narrow so that the end portion of straw 20 will go no further and is held in fixed position therein.

The rear portion of the interior of straw 20 contains wadding 26, usually cotton or some other type of fibre, which may be pressed forward as a piston to force a liquid vehicle medium 30 and an embryo 28 contained therein out of the orifice 14. The straw 20 is of sufficient length to be contained within the longitudinal bore 15 of the tip 10 and the extension of the longitudinal bore 15 within the forward portion of the plunger element 11.

Plunger element 11 generally consists of a hollow stainless steel tube having a plunger rod 22 extending longitudinally therethrough. Plunger rod 22 has a slightly smaller diameter than the internal portion of the straw 20, and inserts into the end portion of straw 20 so as to bear against a wadding 26. Plunger rod 22 extends outside of the rearward portion of plunger element 11 and is connected to a thumb plate 38 upon which thumb pressure is exerted to force plunger rod 22 forward. The rear portion of plunger element 11 has an enlarged flat sides finger grip 36 thereon meant to engage the two fingers of the hand during the time the plunger rod 22 is depressed by the thumb. An orientation mark 24 is placed on finger element 36 with felt marker pen or the like, and is aligned with the orifice 14. Thus when the device is inserted into the host animal, the operator knows the position of the orifice by reference to the orientation mark 24. The flat sides of finger element 36 prevent the device from rolling when set on a smooth surface.

Figures 5, 6:
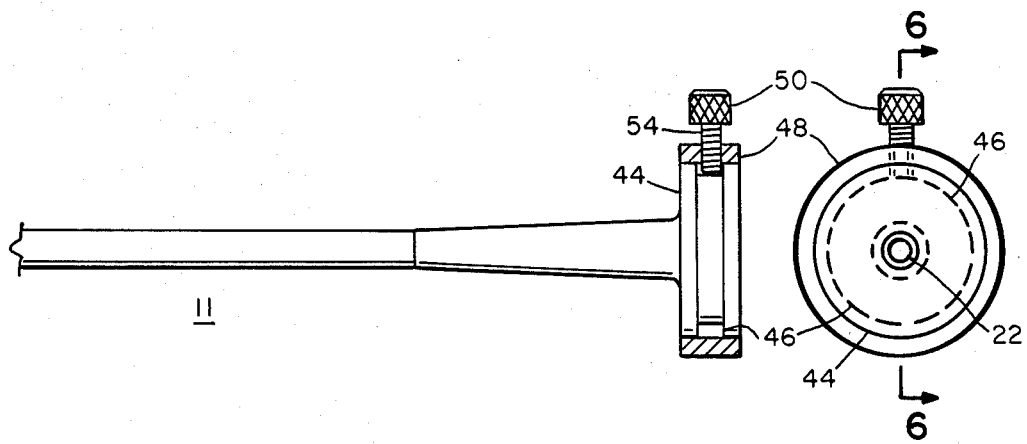
FIG. 5, is a side view of a modification of the plunger portion of the device showing an attachable, rotatable collar with a thumbscrew clamping device.
FIG. 6, is a view taken along lines 6—6 of FIG. 5.

A modification of the device is shown by FIGS. 5 and 6. There a circular fixed head 44 is positioned at the rear end portion of plunger element 11 replacing finger element 36. A circumferential groove 46 is cut in the lateral edge portions of fixed head 44. A rotatable ring 48, having a thumbscrew 50 extending radially therethrough, slips over the fixed head 44. The thumbscrew threads 54 of thumbscrew 50 engage matching threads extending through fixed head 44. When thumbscrew 50 is properly positioned it may be screwed forward in the circumferential groove 46 to bear against the bottom of the groove 46, thus clamping fixed head 44 in position. In operation, the thumbscrew 50 is positioned in the same direction as orifice 14 and is used as a marker to indicate the position of orifice 14. In the operation of the device, it is important that the orifice 14 be positioned within the horn of the uterus in a downward direction so that the embryo 28, within the liquid vehicle medium 30, will be discharged in a way to insure the maximum possibility of pregnancy. Thumbscrew 50 serves as an adjustable mechanical marker to identify the position of orifice 14.

In operation, the tip 10 and plunger element 11 of the device are appropriately sterilized. A straw 20 containing an embryo within a fluid vehicle and having wadding at the end portion thereof, is inserted in the longitudinal bore 15 and forced into the medium bore 34, thus creating a fluid tight seal with the interior lateral surface of the medium bore 34. In this position the end portion of the straw 20 abuts the second section of the shoulders 37 between the medium diamater bore 34 and the small diameter bore 35 and cannot proceed further forward. The tip 10 containing the straw 20 is then screwed into the plunger element 11 utilizing threaded male section 32 of the tip and threaded female section 31 of the plunger element 11. In this position the straw 20 extends within the longitudinal bore of the plunger element 11.

The plunger rod 22 is then inserted in the end portion of the straw 20 adjacent to the wadding 26. The position of the orifice 14 on the tip 10 is then marked by a felt marker pen in the first modification of the device or in the second modification by the thumbscrew 50 positioned on the rotatable ring 48 located on the fixed head 44.

If the rotatable ring 48 is used, the thumbscrew 50 is oriented with the orifice 14 and screwed inwardly against the circumferential groove 46, thus clamping the rotatable ring 48 in position. The tip 10 is then inserted in the animal's vagina, passed through the cervix and into the horn of the uterus. The orifice 14 is then positioned downwardly by noting the position of the thumbscrew 50 in modification 2, or the ink mark in modification 1. The plunger rod 22 is then pressed forward forcing the wadding 26 against the liquid vehicle medium 30 which is forced out of the orifice 14 into the uterus. The device is then carefully withdrawn from the animal.

It should be noted that the countersunk orifice 14 and smooth area of the tip 10 induces little trauma in the animal. Because of the "lock-in" feature of the device, no liquid vehicle medium escapes the end portion of the straw 20. In addition thereto, little mucus collects within said exit passage 17 or exit chamber 16 and the discharge of the embryo 28 is directed in the manner to most favor pregnancy.

We claim:

1. A non-surgical embryo transfer device comprising in combination:
   a longitudinal tip element, having a longitudinal bore partially therethrough, said longitudinal bore in communication with:
   A. a medium bore of lesser diameter than said longitudinal bore adjacent to and in communication with said longitudinal bore;
   B. a small bore of lesser diameter than said medium bore adjacent to and in communication with said medium bore;
   C. an exit chamber positioned within the end portion of said longitudinal tip in communication with said small bore;
   D. an exit passage connected with said exit chamber and leading to the surface of said longitudinal tip;
   a hollow straw adapted to be inserted in said longitudinal bore, having a diameter slightly larger than said medium bore and adapted to be forced within said medium bore to form a tight fluid resistance fit with said medium bore; said hollow straw contains a fluid vehicle therein and is comprised of, in combination:
   an embryo within said fluid vehicle; and
   a wadding positioned within said hollow straw adjacent to said fluid vehicle on the end portion of said straw opposite to said exit chamber;
   a plunger device connected to the end portion of said longitudinal tip element, said plunger device comprising, in combination:
   a plunger rod positioned within said plunger device, the end portion of said rod inserted within the end portion of said straw and adjacent to said wadding;
   a thumb plate attached to the end portion of said plunger rod;
   an enlarged finger grip positioned on the end portion of said plunger device, said finger grip having flat side portions thereon; said finger grip comprising of, in combination:
   a circular fixed head, said circular fixed head having a circumferential groove on the lateral edge portion thereof;
   a rotatable circular ring circumferentially positioned on said circular fixed head;
   a threaded thumbscrew extending through said fixed head and thread engagable therewith, the end portion of said thumbscrew extending within said circumferential groove;
   whereby said fixed head may be rotated about said circular fixed head and clamped thereto by said thumbscrew.

2. The combination as claimed in claim 1, in which said exit passage terminates at a countersunk orifice on the surface of said tip element.

3. The combination as claimed in claim 2, in which said fixed head has a reference mark thereon, said reference mark being oriented with said orifice.

4. The combination as claimed in claim 3, in which said tip and said plunger element are made of a hard smooth substance.

5. The combination as claimed in claim 3, in which said tip and said plunger element are made of stainless steel having a smoothly polished surface.

6. The combination as claimed in claim 5, having
   a shoulder section between said longitudinal bore and said medium bore, said shoulder being inclined at an angle of about 34° to the horizontal;
   a shoulder section between said medium bore and said small bore, said shoulder being inclined at an angle of about 34° to the horizontal.

7. The combination as claimed in claim 6, in which said longitudinal tip element has
   a protruding threaded portion thereon;
   a hollow receptacle at the end portion of said plunger device having internal threads therein, said internal threads adapted to engage the protruding threaded portion of said tip element and to interchangeably engage the threaded portion of any tip element; and
   said hollow straw being a standard ¼ cc artificial insemination straw.

8. A longitudinal tip element with a blunt end portion, said longitudinal tip element having
   a longitudinal bore partially therethrough, said longitudinal bore in communication with:
   A. a medium bore of lesser diameter than said longitudinal bore adjacent to and in communication with said longitudinal bore;
   B. a small bore of lesser diameter than said medium bore adjacent to and in communication with said medium bore;
   C. an exit chamber positioned within the end portion of said longitudinal tip in communication with said small bore;
   D. an exit passage connected with said exit chamber and leading to the surface of said longitudinal tip;
   a hollow straw adapted to be inserted in said longitudinal bore, having a diameter slightly larger than said medium bore and adapted to be forced within said medium bore to form a tight fluid resistance fit with said medium bore; said hollow straw contains a fluid vehicle therein and is comprised of, in combination:
   an embryo within said fluid vehicle; and
   a wadding positioned within said hollow straw adjacent to said fluid vehicle on the end portion of said straw opposite to said exit chamber;
   a plunger device connected to the end portion of said longitudinal tip, said plunger device comprising, in combination:
   a plunger rod positioned within said plunger device, the end portion of said rod inserted within the end portion of said straw and adjacent to said wadding.

9. The combination as claimed in claim 8, in which said exit passage leads to the lateral surface of said longitudinal tip element.

10. The combination as claimed in claim 9, in which said longitudinal tip element has a rounded end portion.

* * * * *